United States Patent [19]
Kerns et al.

[11] Patent Number: 4,756,706
[45] Date of Patent: Jul. 12, 1988

[54] CENTRALLY MANAGED MODULAR INFUSION PUMP SYSTEM

[75] Inventors: Ralph M. Kerns, Laguna Hills; Bernardino Rubalcaba, Jr., Laguna Beach; Donald E. Bobo, Fountain Valley; Kenneth W. Rake, Laguna Niguel; Robert R. Weyant, Claremont; Dennis R. Seguine, Mission Viejo, all of Calif.

[73] Assignee: American Hospital Supply Corporation, Evanston, Ill.

[21] Appl. No.: 821,153

[22] Filed: Jan. 21, 1986

Related U.S. Application Data

[63] Continuation-in-part of Ser. No. 693,771, Jan. 23, 1985.

[51] Int. Cl.⁴ ............................................. A61M 5/16
[52] U.S. Cl. ...................................... 604/66; 604/67; 128/DIG. 13; 364/415
[58] Field of Search .................. 604/19, 21, 30, 31, 604/50–52, 56, 65–67, 82, 83, 246, 251–253, 247; 128/DIG. 12, DIG. 13, 630; 364/413, 415, 416

[56] References Cited

U.S. PATENT DOCUMENTS

| | | | |
|---|---|---|---|
| 3,654,445 | 4/1972 | Mikkelsen et al. | 364/416 |
| 3,723,712 | 3/1973 | Komline, Sr. et al. | 364/413 |
| 4,308,866 | 1/1982 | Jelliffe et al. | 364/413 |
| 4,356,475 | 10/1982 | Neumann et al. | 364/415 |
| 4,392,849 | 7/1983 | Petre et al. | 604/50 |
| 4,483,924 | 11/1984 | Tsuji et al. | 364/415 |
| 4,493,693 | 1/1985 | Bilstad et al. | 128/630 |
| 4,525,775 | 6/1985 | Eydelman | 364/415 |
| 4,546,436 | 10/1985 | Schneider et al. | 364/415 |
| 4,546,770 | 10/1985 | Schlessinger et al. | 128/630 |

FOREIGN PATENT DOCUMENTS 2215331 3/1972 Fed. Rep. of Germany ...... 128/630

OTHER PUBLICATIONS

"Programmable Machine for Dialyser Reuse," *Medical & Biological Engr. & Computing*, 11/80.
"Site," *Microsurgical Systems Inc.*, 1984.

*Primary Examiner*—Stephen C. Pellegrino
*Attorney, Agent, or Firm*—Weissenberger & Peterson

[57] ABSTRACT

A plurality of infusion pump modules are detachably connected to a portable central management unit. The modules can be programmed by the central management unit, and their operating information displayed by the central management unit, when they are connected to it; yet the modules, once programmed, can operate independently when detached from the central mangagement unit, and they can display limited operational information on their own.

14 Claims, 12 Drawing Sheets

PUMP 4
RATE            125.0ML/HR
VOLUME INFUSED      375 ML
VOLUME REMAINING   1125 ML
TIME REMAINING   9 HR 00 MN

RATE | VOLUME | TIME | PIGGYBK | SPECL FUNCT

FIG. 9

PUMP STATUS

OCCLUSION PRESSURE | SET KVO | VOLUME HISTORY
DOSE CALCULATIONS | DELAYED START |

- 290
- 292, 218, 246
- 216 VOLUME HISTORY
- LAST 24 HR  00 MN
- TOTAL  4680 ML
- PUMP 1  1200 ML    PUMP 2  1500 ML
- PUMP 3  840 ML     PUMP 4  1400 ML
- HISTORY TIME
- PUMP STATUS
- SPECL FUNCT — 226

FIG. 15

- 300, 218, 220, 272, 246
- 216 VOL HISTORY TIME
- 24 HR  00 MN
- 214 ENTER TIME  HR  MN
- Keypad: 1 2 3 / 4 5 6 / 7 8 9 / HR 0 MN
- CLEAR, PUMP STATUS, ENTER, SPECL FUNCT
- 224, 226

FIG. 16

- 310, 314, 246
- 214 SELECT A PARAMETER
- 312 DOSAGE PP UG/KG/MN
- RATE PP ML/HR
- 316 DRUG PP UG
- 216 SOLN VOL PP ML
- 370 WEIGHT PP KG
- Keypad: 1 2 3 / 4 5 6 / 7 8 9 / . 0 CLR
- ENTER, PUMP STATUS, SPECL FUNCT
- 318, 220, 224, 226, 218

CENTRALLY MANAGED MODULAR INFUSION PUMP SYSTEM

This application is a continuation-in-part of application Ser. No. 693,771, filed Jan. 23, 1985, now abandoned, and entitled "Centrally Managed Modular Infusion Pump System".

This invention relates to modular infusion pumps, particularly to a system permitting the central management of individually operable infusion pumps and other sensing or control units.

BACKGROUND OF THE INVENTION

Infusion pumps and sensing devices such as blood pressure monitors and oxymeters are in widespread use in the medical field. Some infusion pumps currently in use also permit the infusion of several medications at different rates through a common cannula from a single unit with multiple pumps.

In the environment of intensive care units, cardiac care units, operating rooms or trauma centers, it is often necessary to infuse into the patient one to eight different drugs simultaneously. In addition, some of the drugs used in these environments are not directly compatible with each other and therefore need to be infused into the patient at different points of the body. Also, it is frequently necessary to observe and recall the condition of the patient at certain intervals or to adjust the medication in accordance with the patient's reaction to it. In order to avoid errors due to the proliferation of individual pieces of equipment around a seriously ill patient, it is highly desirable to manage the infusion and monitoring functions from a central point; yet it is often necessary to transport the patient during the intravenous administration of medication under circumstances where it is impractical to transport an entire centrally controlled system together with the patient.

SUMMARY OF THE INVENTION

The present invention solves the problems outlined above by providing a modular system in which pump and monitoring modules can be selectively attached, both physically and electrically, to a central management unit. The central management unit controls the internal setup of all modules attached to it, and receives and displays information from them. Each of the modules, however, is capable of being detached from the central management unit, and while so detached is capable of operating independently for an extended period of time. During this period, the detached unit internally maintains records which assure an accurate display once it is reattached to the central management unit.

In order to prevent confusion of data due to the detachment and reattachment of modules in possibly different orders, the central management unit of this invention automatically keeps track of the identity of various modules regardless of their position in the module stack attached to the central management unit.

In another aspect of the invention, a special IV stand is provided for maintaining the various medications and their infusion cannulae in such physical arrangement as to prevent accidental confusion of the modules with one another.

In still another aspect of the invention, the central management unit is equipped with a display screen which also serves as a keyboard. The screen is flat and is surrounded by a bezel with aligned openings attached to receive light-emitting diodes and phototransistors mounted, respectively, on flexible conduit strips for easy alignment of a grid pattern of light beams which, when interrupted by a finger touching the screen, trigger selected control functions of the central management unit.

It is therefore the object of the invention to provide a portable centrally-managed integral set of selectably removable modular units for pumping and monitoring purposes, each unit being adapted to be programmed and monitored through the central management unit but being capable of functioning independently when detached therefrom.

DESCRIPTION OF THE DRAWINGS

FIG. 2b is a partially broken away detail view of a portion of FIG. 2a;

DESCRIPTION OF THE PREFERRED EMBODIMENT

Figure 1:
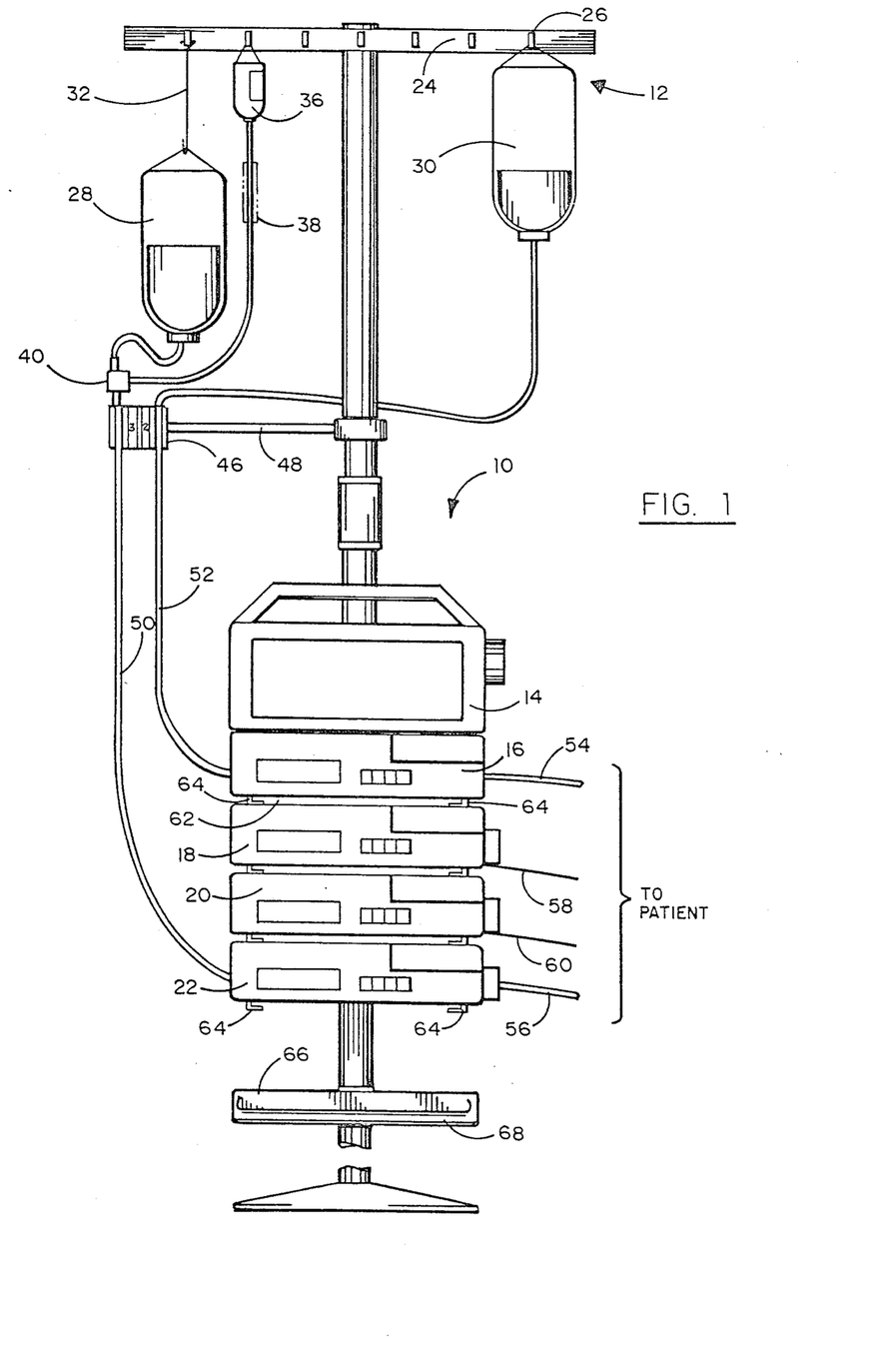
FIG. 1 is a front elevation of an IV stand constructed in accordance with this invention and supporting the modular pump system of this invention including a central management unit and four modules.

FIG. 1 shows the modular system of this invention generally at 10. In FIG. 1, the system 10 is shown attached to an IV stand 12 specially designed for use with the modular system 10.

The system 10 consists of a central management unit 14 which is permanently attached to an infusion pump unit 16. In addition, the system 10 as illustrated in FIG. 1 includes three removable modules which, for the purposes of this description, may be a blood pressure monitor 18, an oxymeter 20, and a second infusion pump module 22. It will be understood that the type and number of modules in the system 10 is limited only by the physical and electrical ability of the wiring and of the central management unit 14 to handle the desired types and numbers of modules.

In the embodiment of FIG. 1, the IV stand 12 has a main support bar 24 equipped with hooks 26 from which IV bottles 28, 30 can be suspended. A piggyback bottle 36 may be connected through a burette 38 to a check valve 40 which causes the piggyback medication to be substituted for the fluid from the main IV bottle 28 until the piggyback bottle 36 is exhausted. If this is done, the main IV bottle 28 must be suspended below the piggyback bottle 36 by an extension wire 32 so that the hydraulic head of the piggyback bottle 36 will be greater than that of the main bottle 28.

To prevent the mutual crossing of the cannulae feeding the pump unit 16 and 22, a guide plate 46 is positioned at the end of an arm 48 extending from the stand 12. The guide plate 46 contains a sufficient number of guide slots to hold each of the cannulae leading to a modular unit of the stand 10 in a position where the cannulae do not cross each other. It should be kept in mind that the cannulae 50, 52 are typically of standard length, and the support bar 24 and guide plate 46 are so positioned that the length of each cannula 50, 52 from the IV bottle 28 or 30 to the module 16 or 22 is essentially the same.

The output of pump modules 16 and 22 consists of cannulae 54, 56 respectively. The input of blood pressure monitor 18 and oxymeter 20 consists of cables 58, 60 respectively.

As will be discussed in more detail hereinafter, the modules 18, 20 and 22 are selectively attachable to the central management unit 14 and its pump module 16 by sliding the flanged plate 62 at the top of each module into the channels formed by the flanged rails 64 on the underside of the module above it. Because it may be desired, for example, to remove an intermediate module such as the oxymeter 20 from the stack, a shelf 66 is provided on the IV stand 12. For removal of the module 20, the module 22 is first removed from the stack and placed on the shelf; the unit 20 is then removed; and the unit 22 is then picked up from the shelf 66 and slid into position underneath unit 18 in place of unit 20. Handle 68 may be provided on shelf 66 to pull the wheeled stand 12 around as necessary.

Figure 2A:
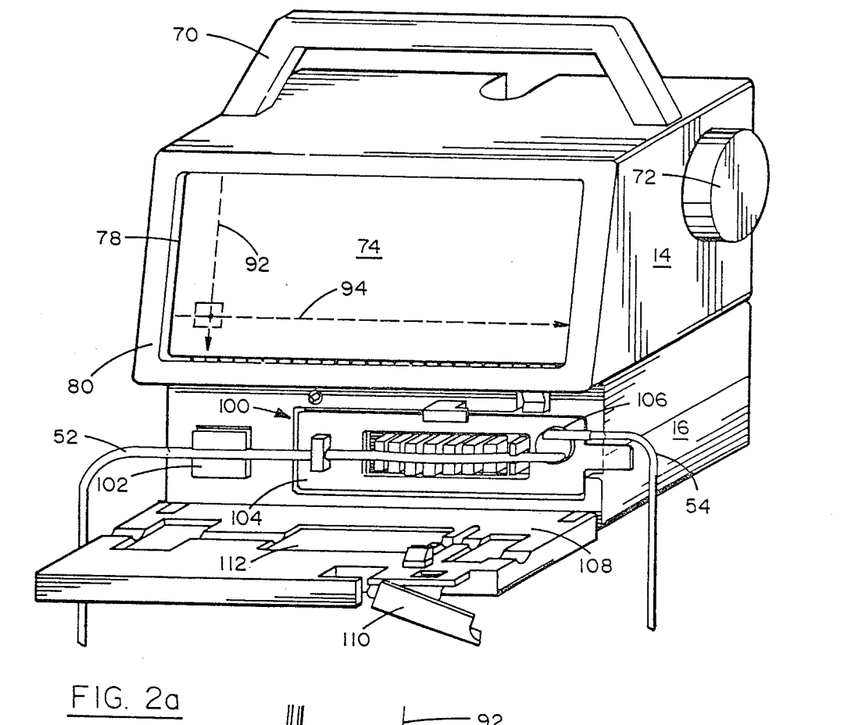
FIG. 2a is a perspective detailed front view, showing the central management unit and first pump module with its door open.

FIG. 2a shows the central management unit 14 and the #1 pump unit 16, which is permanently attached to it, in greater detail. The central management unit 14 can be carried by handle 70 and can be attached to the pole of the IV stand 12 by a clamp operated in a conventional manner by knob 72. The central management unit 14 has a flat screen 74 on which various information can be displayed as hereinafter discussed.

Figure 2B:
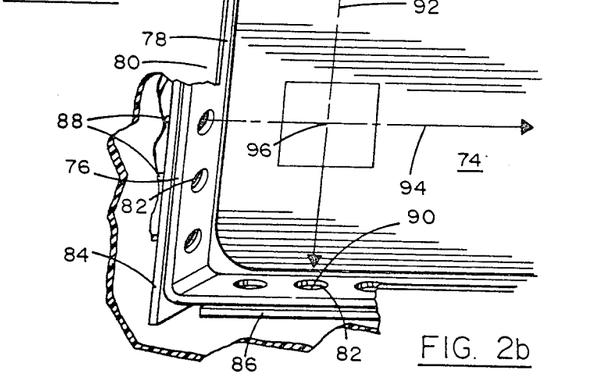

As best shown in FIG. 2b, a bezel 76 surrounds the edge of the screen 74 in the slot 78 formed by housing 80. The bezel 76 is provided with spaced openings 82 which are aligned on opposite sides of the screen 74. Flexible conductor strips 84, 86 are attached to the rear surface of the bezel 76. On one long side and one short side of the screen 74, these conductor strips carry LEDs 88 which are aligned with the openings 82 in bezel 76, whereas on the other two sides of the screen, the conductor strips carry phototransistors 90 which are also aligned with the openings 82 in the bezel 76. The LEDs 88 are energized, and their opposing phototransistors 90 enables, in a serial manner at a rapid scanning rate, so that any scattering of light cannot confuse the uniqueness of each light beam 92, 94 whose intersection 96 defines any particular location on the screen 74.

Thus, placement of an operator's finger on the area 98 of the screen 74 will result in the simultaneous interruption of light beams 92 and 94. This simultaneous interruption can then be interpreted in a conventional manner by the electronics of the central management unit 14 as an instruction to execute or enter whatever command or number is being displayed in the area 98.

The pump unit 16 is of generally conventional construction as far as the peristaltic pump 100 is concerned. The cannula 52 is clamped in a bubble sensor 102 and is then held against the peristaltic pump 100 by a cartridge 104 which also contains a pressure dome 106. From the pressure dome 106, the cannula 54 extends toward the patient. When the door 108 of pump 16 is closed and locked by way of the handle 110, the cartridge 104 and cannula 52 are pressed against the pumping fingers of the peristaltic pump 100 by the pressure plate 112.

Figure 3:
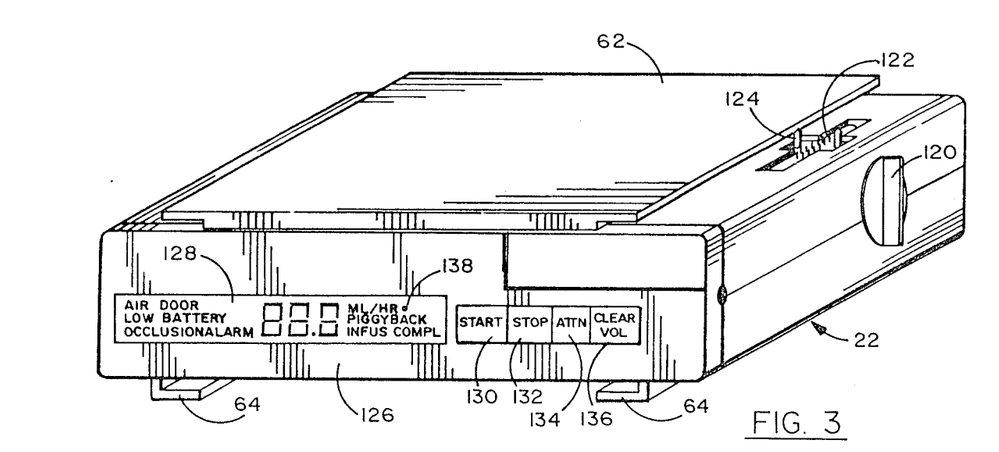
FIG. 3 is a perspective detail front view of a pump module with the door closed.

FIG. 3 shows the details of a removable pump module such as 22. As previously noted, the module 22 attaches to the stack by sliding the support plate 62 into the channels 64 of the unit above it. An electrical connection between the unit 22 and the unit above it (e.g. unit 20) is then established by turning knob 120 which causes the male contact pins 122 and the guide pins 124 to be raised into mating contact with a corresponding set of female contact pins 125 and recesses 158 (FIG. 4) on the underside of the unit above.

The front panel 126 of the module 22 contains a display screen 128 and a set of control buttons 130, 132, 134, 136 whose function will be described below. The display screen 128 displays the delivery rate of the module 22 as well as status information regarding the operation of the module. This status information may preferably consist of an indicator 138 which may flash to indicate that the pump is running, and of the following other indicators:

"AIR" to indicate that air has been detected in the cannula;

"DOOR" to indicate that the door 108 is not tightly closed;

"OCCLUSION" to indicate an occlusion in the cannula 54;

"ALARM" to indicate a pump malfunction;

"PIGGYBACK" to indicate multimedication status;

"INFUS COMPL" to indicate the completion of a programmed regimen of infusion.

The start button 130 is arranged to start the peristaltic pump 100 unless the unit 22 is in delay mode as explained hereinafter, in which case the delivery rate indication alternates with the indication "dly" until such time as the pump actually starts. The pump 100 may be stopped at any time by pressing the STOP button 132.

The ATTN button 134 causes a signal to be sent to the central management unit 14 which in turn causes information regarding the status of unit 22 to be displayed on the screen 74 for alteration or setting as necessary. The unit 22 accumulates a running total of the infusion volume delivered by the pump 100. This running total can be cleared by pressing the CLEAR VOL button 136.

FIGS. 4a through 4d illustrate the functioning of the electrical interconnection and physical interlocking mechanism previously alluded to in the description of FIG. 3. The knob 120 turns a cam 140 which engages a shoulder 142 (on the upstroke) or 144 (on the downstroke) of the carriage 146. The carriage 146 is vertically movable in guides 148 formed in the body of the modular unit in which it is located.

At its top, the carriage 146 supports a connector block 150 and a pair of guide pins 152. The connector block 150 contains the male contact pins 122 of the electric connection between modules. The guide pins 152 extend substantial distances above the surface of the connector block 150 so as to guide the connector block 150 into precise alignment with the connector block 156 of the unit above (which contains the female contact pins 125) when the guide pins 152 mate with the recesses 158 of the unit above. When the connector block 150 is retracted, the guide pins 152 are withdrawn into the module housing.

It will be noted that when the guide pins 152 engage the recesses 158, the two connected modules are physically locked together and cannot be pulled apart. The connector block 150 and guide pins 152 are fixed with respect to one another, but their combined assembly is mounted for limited movement on carriage 146 so that any minor misalignment between the units being connected can be compensated for.

Figure 4A:
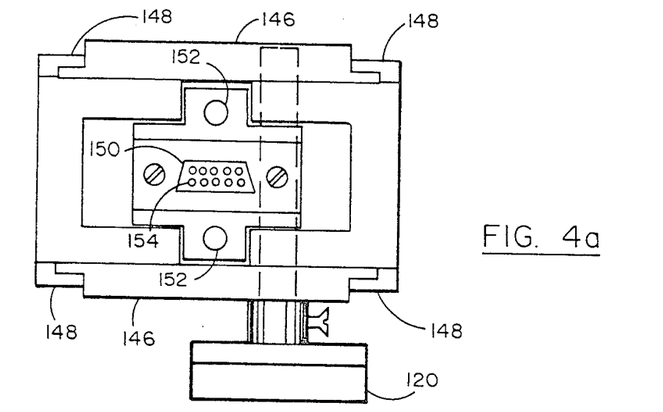
FIGS. 4a, b, c, d and e are partly schematic elevations illustrating the physical and electrical interconnection of the modules within the stack.
Figure 4B:
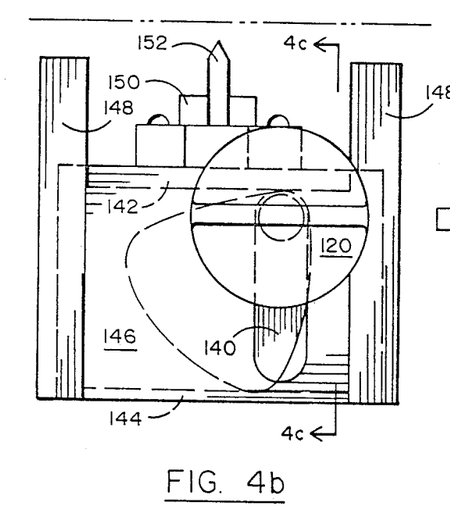
Figure 4C:
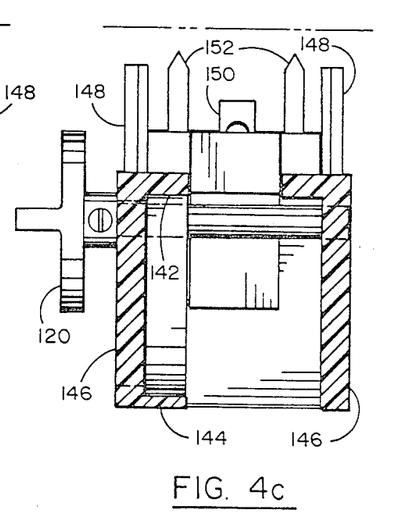
Figure 4D:
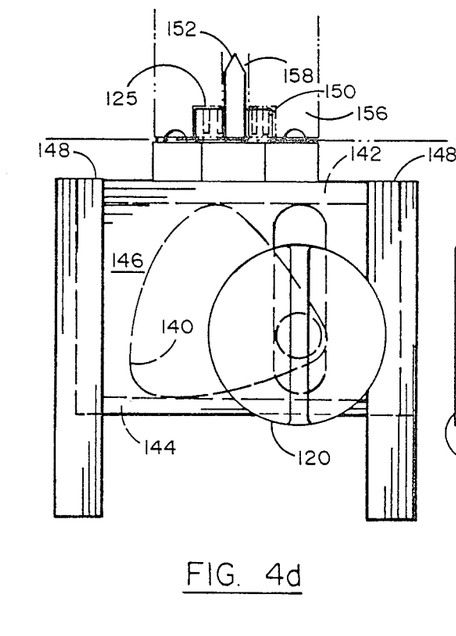
Figure 4E:
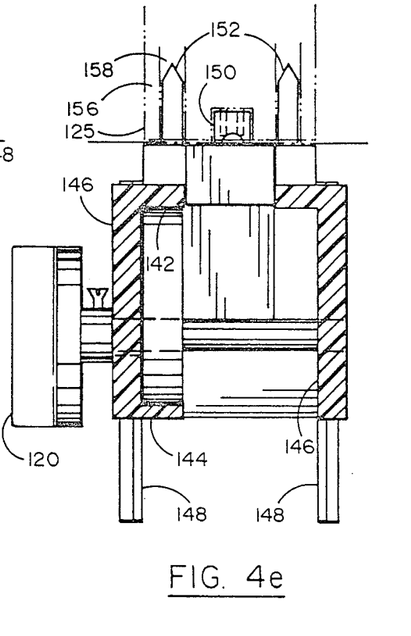
Figure 4F:
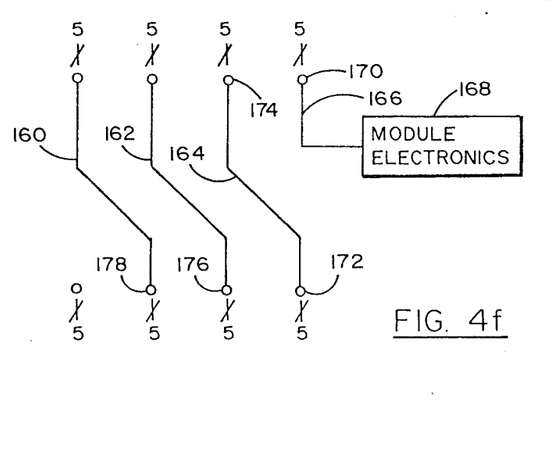
FIG. 4f is a schematic diagram illustrating the electrical interconnections between the connector blocks of a module.

As shown in FIG. 4e, the electrical interconnection between the male connector block 150 and the female connector block 156 of the same module may consist of 20 lines arranged in four cables 160, 162, 164 and 166, each consisting of five wires representing, respectively, the ground, AC+, AC−, incoming communication, and outgoing communication leads. It will be noted that the cable 166, to which the module electronics 168 are connected, originates from the contact group 170.

In the module below the module shown, the contact group 170 would mate with the contact group 172 of the module shown. Likewise, the contact group 174 of each module mates with the contact group 176 of the module above, and so forth. In this manner, the contact group 172 in the bottom of the permanently attached module 16 will always be connected to the electronics of the next lower module (in this case module 18); the contact group 17 will connect to the electronics of the third module (in this case module 20); and the contact group 178 will connect with the electronics of the fourth module (in this case module 22).

It will be noted in the foregoing description that the identity of a module which is connected to any given one of the contact groups 176, 178 at the bottom of the permanently attached module 16 depends not on the identity of the module itself, but on the position it occupies in the module stack. Consequently, it is necessary for each module to have an identification which is recognizable by the central management unit 14 regardless of the position of the module within the stack. To accomplish this, each module is given an identification code by the central management unit 14 when it is first programmed. The module retains this code in its memory and transmits it periodically to the central management unit 14.

The unit 14 displays on its screen the data relating to various units in the stack under a heading (e.g. "Pump 4") designating the position of the unit within the stack. Consequently, when a unit is removed from the stack and later reinserted into the stack in a different position, the central management unit 14 will recognize the mismatch between the unit identification code and its stack position and make an appropriate transfer of information in its memory to take into account the new stack position of the replaced unit.

Figure 5:
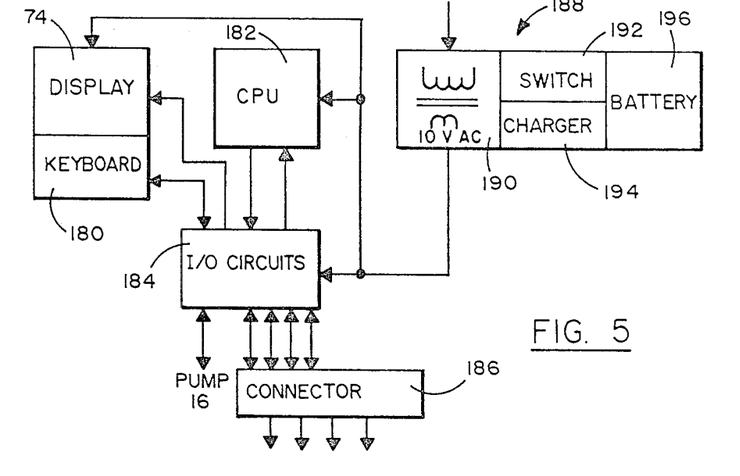
FIG. 5 is a block diagram of the central management unit.

As shown in FIG. 5, the electronics of the central management unit 14 consist essentially of the display screen 74, a keyboard 180 (which may be either physical or one of the displays on the screen 74, or both); a microprocessor 182; input/output circuits 184; a connector 186 (which is physically located on the underside of pump 16); and a power supply 188 consisting of a transformer section 190, an AC/battery switch, a battery charger 184 and a battery pack 196. Normally, the power supply 188 would be connected to a commercial 110V AC supply. The transformer section 190 isolates the modular system 10 from the power network and provides AC power to the central management unit 14 and to all the modules at a safe 10V level. The charger 194 maintains the battery 196 in a charged condition so that it will be ready to take over the power supply for the management unit 14 and the permanently attached unit 16 if the commercial power fails and the switch 192 automatically places it into the circuit.

The microprocessor or central processing unit 182 continually interrogates the module 16 directly through the I/0 circuits 184, and the other units indirectly through the connector 186, in a serial manner and stores information received from them in its memory. An alarm indication is provided on the central management unit 14 if the microprocessor 182 sees a module in the stack which it cannot identify or with which it cannot communicate. The microprocessor 182 through the I/0 circuits 184, also actuates the display 74 and responds to information from the keyboard 180 such as the interruption of selected light beams 92, 94 (FIG. 2) associated with elements of the key pad 218 (FIGS. 7-17) displayed on the touch screen 74.

For example, if it is decided to program a new pump module such as module 22 just inserted into the stack, the ATTN button 134 on module 22 is pressed. This causes module 22 to send a signal to microprocessor 182 to display on the screen 74 a display entitled "PUMP 4" and providing information on the delivery rate, the volume to be infused and the keep-vein-open rate (i.e. the emergency rate to be used in a low battery situation or when an infusion is completed), together with a key pad for entering that information. By touching appropriate portions of the screen, the requisite information can be entered and eventually transmitted by the microprocessor 182 to the internal memory of the pump unit 22. Simultaneously, the selected parameters are displayed on the screen 74 for confirmation.

Likewise, the microprocessor 182 collects and retains operational information from each module at frequent intervals and displays the history of each module's operation on demand for any selectable period of time. The microprocessor 182 can also be programmed in accordance with known techniques to calculate the rate of infusion, given the concentration of medication in the IV solution, the dosage per pound of body weight required, and the weight of the patient. Furthermore, the microprocessor 182 can be programmed by known techniques not only to display a graphic history of patient body parameters such as blood oxygenation sensed by the oxymeter 20, but also to receive information such as blood pressure information from the module 18 and to adjust the delivery rate of blood pressure control medication through a selected module in response to it.

Figure 6:
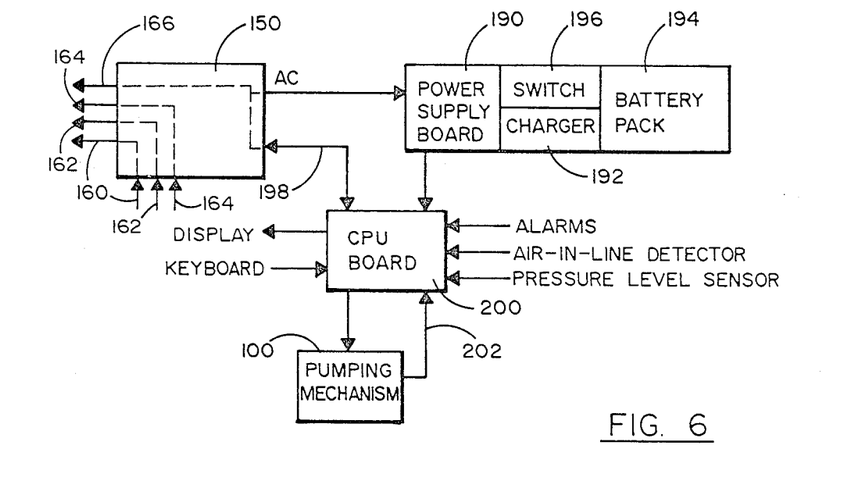
FIG. 6 is a block diagram of a pump module.

The internal electronics 108 (FIG. 4e) of a pump module such as 22 are shown in more detail in FIG. 6. From the connector block 150, AC power is supplied to a power supply board 190 which produces bias voltages for the modular electronics in a conventional manner. As in the central management unit 14, the power supply board 190 operates a battery charger 192 connected to a battery pack 194 which automatically substitutes itself for the AC power supply, through the action of switch 196, when the module is disconnected from the stack or the AC power fails for another reason.

The incoming/outgoing communication lines 198 are connected to the CPU board 200 which operates the display 128 on the front of the module and stores and transmits data regarding the operation of the module. The CPU board 200 operates the actual pumping mechanism 100 in accordance with the commands received from central management unit 14 and stored in the memory of the CPU board 200, and in accordance with the feedback 202 received from the pump mechanism 100 to indicate its operational status. Other imputs to the CPU board 200 may be the inputs from control buttons 130 through 136 discussed above, as well as from conventional pressure level sensors, air-in-line detectors (such as the bubble sensor 106, FIG. 2a), or other alarm condition detectors associated with the mechanics of the pump.

The details of the battery operation in the module 22 are the subject of copending application Ser. No. 661,352 filed Oct. 15, 1984, and the details of the control of pumping mechanism 100 are the subject of copending application Ser. No. 660,940 filed Oct. 13, 1984.

Because the pumping mechanism 100 is operated by a stepping motor whose stepping rate is controlled by the CPU board 200, it is possible for the CPU board 200 to keep an exact count of the fluid volume delivered by the pumping mechanism 100. The CPU board 200 retains in its own memory the total amount of fluid delivered, so that the pump 22 can shut off when the infusion is complete even though it is detached from the central management unit 14. While connected to the management unit 14, the CPU board 200 continually transmits delivery data to the central management unit 14 so that the latter can keep track of the delivery history of pump 22.

The CPU board 200 is also equipped with a clock so that the start of the fluid delivery may be delayed until a predetermined future time under the control of the central management unit 14. Conversely, the CPU board 200 can actuate an alarm if, prior to a delayed start, an occlusion or other alarm condition occurs which would prevent the scheduled start of delivery in the delay mode.

It will be seen that the foregoing invention provides a versatile tool for the central management of multiple intravenous infusions. Because of the central management feature and the centralized recording of each unit's operational history, potentially dangerous errors are avoided and the work of medical personnel in complex situations is greatly facilitated; yet transportation of a patient with only one or a few of the multiple infusions is made possible without upsetting the central management feature.

Operation

The operation of the modular device of this invention in connection with pump modules is as follows:

To program one of the pump modules such as 22 (FIG. 1), the ATTN button 134 on the module 22 (FIG. 3) is first pressed. The ATTN command is encoded and stored within the module 22 and is transmitted to the central management unit 14 when the module 22 is next interrogated by the central management unit 14 as described above. Receipt of the ATTN command causes the central management unit 14 to display an entry screen 210 (FIG. 7) on the display 74. In its left half, the entry screen 210 contains an identifier line 212, an entry line 213, and status lines 216. In its right half, the entry screen 210 contains an entry key pad 218 including numerical keys 220, function keys 222, and an entry bar 224. The identifier line shows the type of unit (i.e. PUMP) and its position in the stack (as determined by the cable 160, 162, 164, or 166 in FIG. 4f on which the ATTN signal appears). The entry line shows SELECT FUNCTION if no function has been selected, or the function (e.g. VOLUME ) which has been selected for entry by touching one of the function keys 222. The status lines show the current status of all the available functions.

Figure 7:
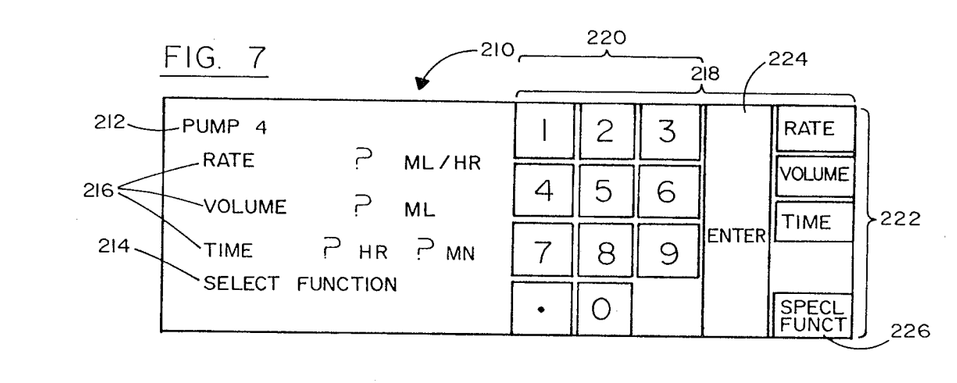
FIGS. 7 through 17 depict screen displays on the CMV, illustrating the operation of the apparatus of this invention.

Entry of the numerical parameters for the desired function via the keypad 218 causes the entered value to appear in the entry line 214 as it is entered. Touching the entry bar 224 then returns the entry line 214 to SELECT FUNCTION and substitutes the selected parameter for the question mark in the appropriate status line 216.

Figure 8:
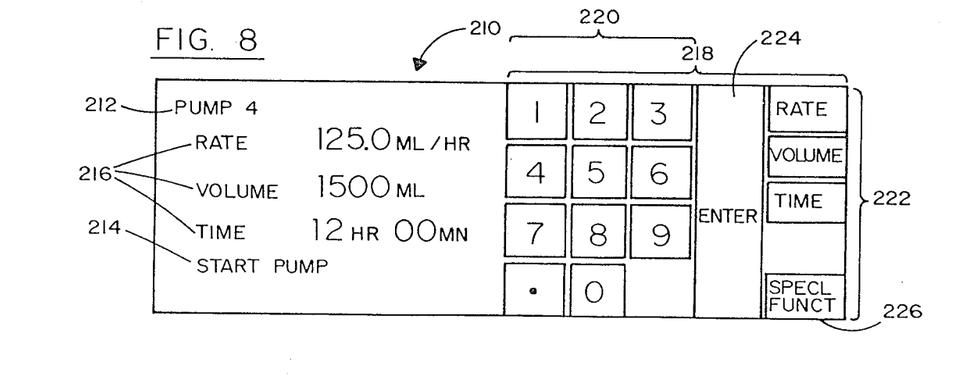

When both volume and either time or rate have been entered, the status lines 216 display the selected volume and rate parameters (time is eliminated from the status lines 216), and the entry line 214 goes to START PUMP (FIG. 8). At this time, the pump 22 may either be started, or special functions as discussed hereafter may be selected, or other units may be set by pressing their ATTN button 134.

Starting a pump such as 22 by pressing the START button 130 (FIG. 3) causes the status screen 230 (FIG. 9) to appear whenever pump 22 is in the ATTN mode (each module remains in the ATTN mode until the ATTN button 134 on another module is pressed). The status screen 230 shows the rate (as entered directly or as computed from volume and time entries), volume infused, volume remaining, and time remaining. The values of the latter three parameters are supplied by the internal memory of the CPU 182 (FIG. 5) of central management unit 14, which is continuously updated from the internal memory of CPU board 200 (FIG. 6) of module 22 each time the module 22 is interrogated by the central management unit 14 as previously described. The CPU 200 is in turn updated by the pumping mechanism 100 over line 202.

When the parameters have been set for a pump such as 22, the display 128 (FIG. 3) of the pump module 22 shows the rate, as well as an indicator symbol 138 which flashes when the pump 22 is running but is not displayed when the pump 22 is stopped.

Figure 9:
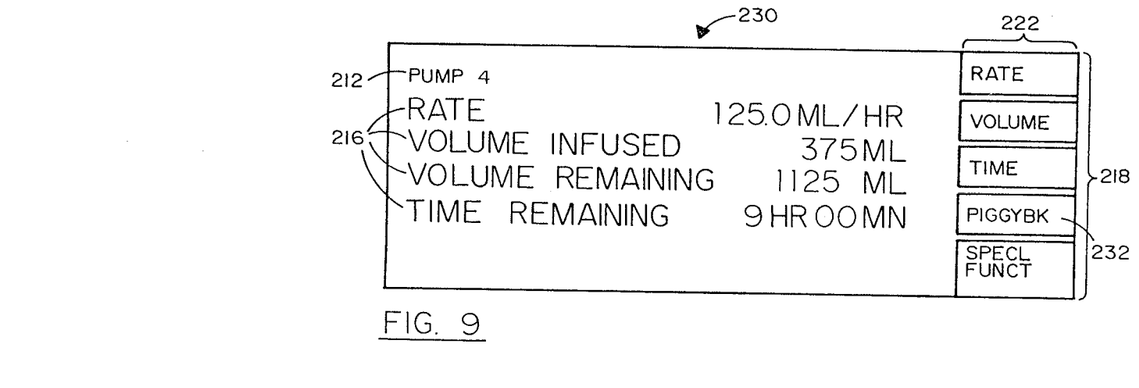

The volume, rate, time and special function keys designated as 222 in FIGS. 7 and 8 continue to appear in the status screen 230 and may be used to return to the entry screen 210 for the purpose of changing any of the parameters controlled by those keys.

The status screen 230 contains an additional function key 232 labeled PIGGYBACK ON. If the key 232 is touched, the pump 22 stops, and the entry screen 210 reappears with the notation PIGGYBACK following the module's stack location. Parameters for a piggyback delivery may now be set as described above. When started, the pump 22 will complete the piggyback delivery and then automatically switch back to complete the interrupted primary delivery. During the operation of the pump 22 in piggyback mode, the status screen 230 also shows the notation PIGGYBACK following the legend PUMP 2, and the values of the parameters displayed are the piggyback values.

Figure 10:
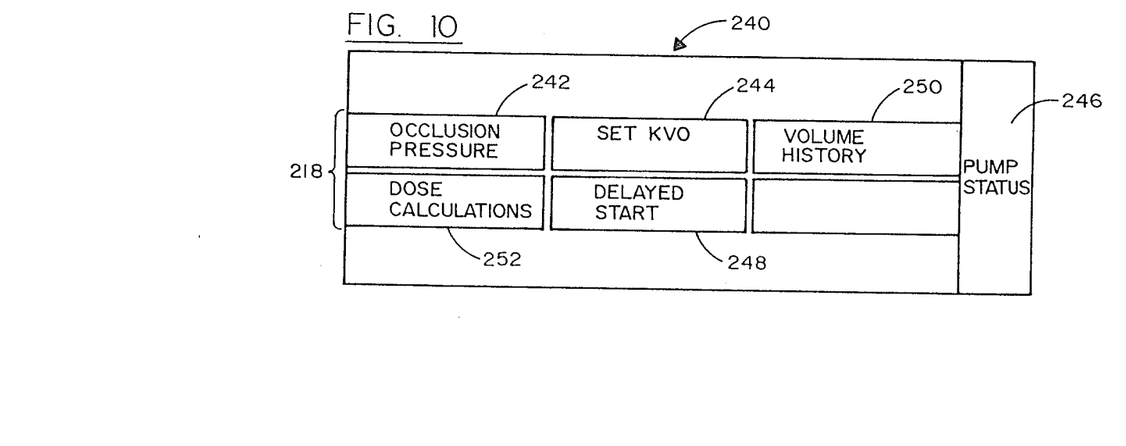
Figure 11:
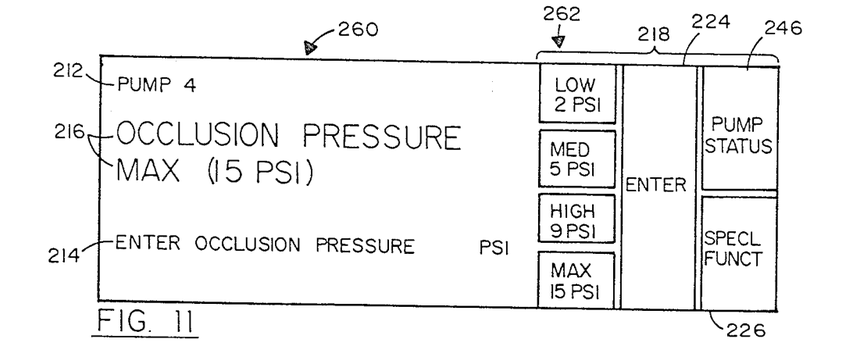

Touching the SPECIAL FUNCTIONS key 226 at any time produces the special functions screen 240 (FIG. 10). The occlusion pressure (i.e. the back pressure at the output of the pump which will cause the pump to stop and alarm) may be set by touching the OCCLUSION PRESSURE key 242, and the keep-vein-open rate (i.e. the rate at which the pump will operate in a low-battery situation or during a temporary interruption of the normal delivery) may be set by touching the SET KVO key 244.

Normally, occlusion pressure and KVO rate are automatically set to default values of 15 psi and 3 ml/h, respectively. No indication is given of that fact. If, however, occlusion pressure or KVO rate is set to a non-default value, then the chosen pressure and rate are shown at the bottom of the entry screen 210 and status screen 230.

Touching the OCCLUSION PRESSURE key 242 causes the pressure selection screen 260 (FIG. 11) to appear. Its special number keys 262 allow the selection of four approximate values which are entered by touching the entry bar 224. Touching the SPECIAL FUNCTIONS key 226 brings back the special functions screen 240 (FIG. 10), while the PUMP STATUS key 246 returns the display 74 to the entry screen 210 or status screen 230 as then appropriate.

Figure 12:
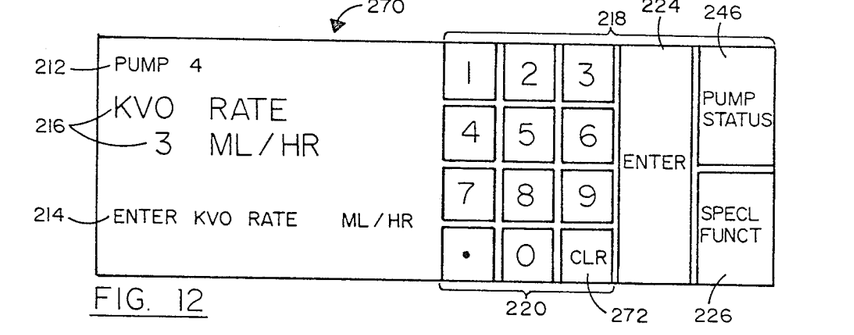
Figure 13:
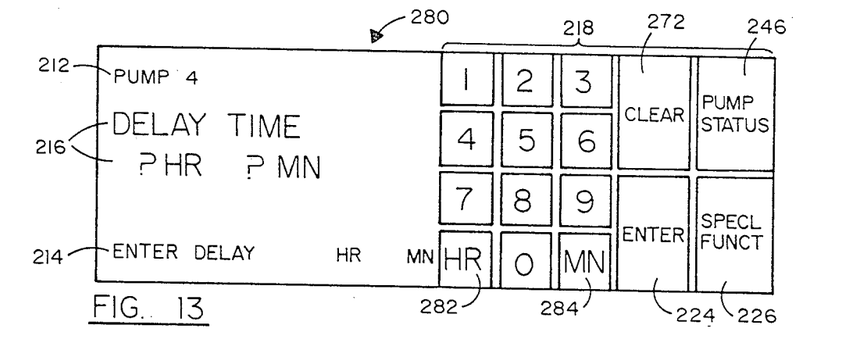

Touching the SET KVO key 244 produces the KVO rate screen 270 (FIG. 12). The key pad 218 of this screen contains, in addition to the entry bar 224 and the pump status and special function keys 246, 226, number keys 220 which differ from those of FIGS. 7 and 8 only in the provision of an additional CLEAR key 272 for clearing an erroneous keystroke prior to entry. As in the entry screen 210, the entry line 214 records the keystrokes as they are made. When the entry bar 224 is touched, the entry line 214 disappears, and the value shown therein is transferred to the status line 216.

If a delayed start of the infusion is desired, the DELAYED START key 248 of FIG. 10 is touched. This produces the delayed start screen 280 (FIG. 13), in which the numeric keys 220 are supplemented by hour and minute keys 282, 284 but otherwise function in the same manner as described above, for the entry of a time value. The entry of a delay time causes that time interval to be inserted between the pressing of the START button on the selected pump and the actual starting of the pump.

Figure 14:
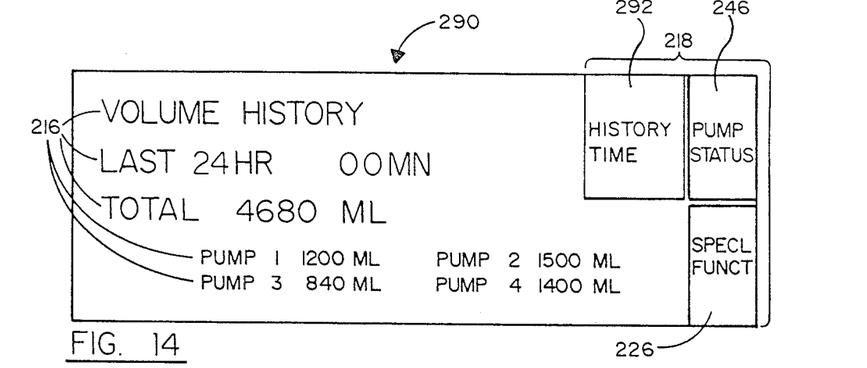

The apparatus of this invention is capable of providing an indication of the volume infused by individual pumps such as 16 and 22, as well as by the apparatus as a whole, for a selectable period of time. The period consists of a selectable (in increments of five minutes) interval ending at the time of the indication request. The request is initiated by touching the VOLUME HISTORY key 250 (FIG. 10), which produces the volume history screen 290 (FIG. 14).

It will be noted that unlike the previously described screens, the volume history screen 290 does not have a module identification line. The reason for this is that the screen 290 gives information for all modules, regardless of whether or not they are in the ATTN mode.

The status lines 216 of the screen 290 give the following information: (a) the length of the period (the default value being the time elapsed since the central management unit 14 was first turned on, or 24 hours, whichever is less); (b) the total volume dispensed (which, for reasons detailed hereafter, may differ from the sum of the individual pump volumes shown); and (c) the volumes infused by the individual pumps during the period.

It should be noted that the CPU 182 of central management unit 14 keeps track of the operation of individual pumps by their individual identification numbers, not by their position in the stack. Consequently, if at the time of the volume history request, three pumps are connected to the central management unit, and a fourth pump was at one time connected to the central management unit but is now removed, the PUMP 2 and PUMP 3 values are the values for the pump modules in stack positions 2 and 3, respectively, at the time of the request, even though they may have been elsewhere in the stack at other times. Pump 16 (FIG. 1) is always in the PUMP 1 position, as it is permanently attached to the central management unit 14. The volume infused by the removed pump up to the time of its removal is not displayed but is retained in the memory of the central management unit 14.

Figure 15:
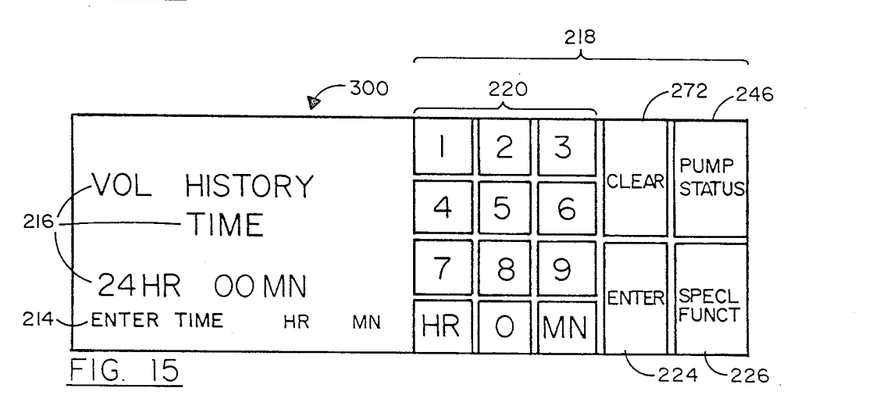

The HISTORY TIME key 292 in screen 290 (FIG. 14) may be used to change the volume history period. Touching it produces the history time selection screen 300 (FIG. 15). Selection of the volume history period by that screen takes place in the same manner as the selection of the delay time described above in connection with FIG. 13. Touching the ENTER key 224 on screen 300 returns the display to the volume history screen 290 of FIG. 14.

The apparatus of this invention permits the direct calculation of any dose parameter from the other dose parameters. Specifically, the dose parameters involved in the calculation are dosage (in $\mu$g, mg, or g of drug per kg of body weight per minute), the total amount of drug infused (in $\mu$g, mg, or g, the patient's body weight (in kg, lb or g), the infusion rate (in ml/hr), and the total volume of solution infused (in ml).

The weight parameter may or may not enter into a dose calculation. Consequently, unless weight is entered as one of the first three known parameters, it is ignored and the dosage parameter is displayed in $\mu$g per minute unless otherwise set as outlined below.

Figure 16:
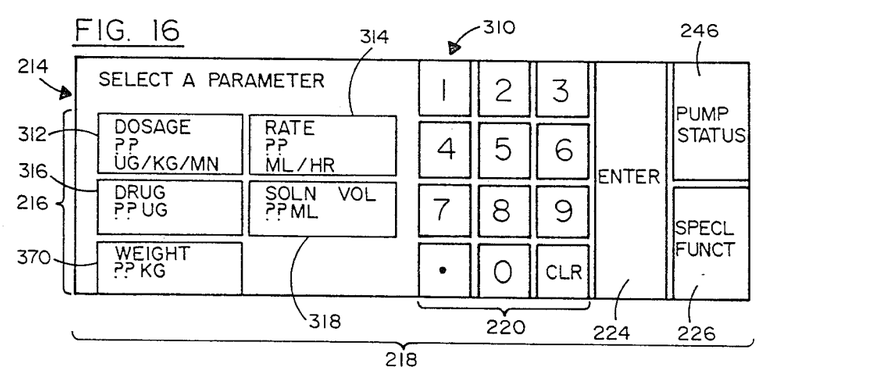
Figure 17:
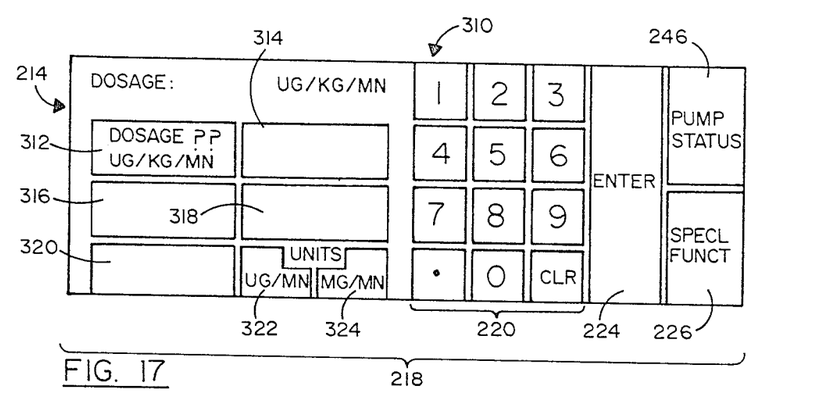

Touching the DOSE CALCULATIONS key 252 on the special functions screen 240 (FIG. 10) produces the dose parameter selection screen 310 (FIG. 16). In that screen, the entry line 214 directs the selection of a parameter by touching one of the parameter keys 312 through 320. When this is done the remaining parameter keys go blank and the entry line 214 displays the selected parameter (FIG. 17). In addition, if the selected parameter is dosage, drug amount, or weight, appropriate units keys 322, 324 appear to select a desired unit. The selectable units are as follows: for dosage, $\mu$g/min or mg/min (touching either of these causes the weight key 320 to disappear entirely), with a default of $\mu$g/kg/min; for total drug amount, mg or g, with a default of $\mu$g; and for body weight, lb or g, with a default of kg.

Following the entry of a parameter, the blank parameter keys and the entry line 214 return to their FIG. 16 condition, with the entered value appearing in its parameter key. When three parameters (or four parameters if weight was one of the first three) have been selected and entered, the entry line 214 displays a series of question marks, and the computed fourth or fifth parameter value appears in its parameter key. If weight is not involved in the calculation, the weight key 320 disappears from the screen 310. The calculated value may be recorded and used in the programming of a pump by touching the PUMP STATUS key 246 to return to the entry screen 210 (FIGS. 7, 8) or the status screen 230 (FIG. 9).

It will be understood that the operational sequence described above, including the positioning of lines and keys on the display 74 (FIG. 1), as well as the interpretation of the interruption of light beams such as 92, 94 (FIG. 2) by the touching of selected portions of the display 74, is accomplished by programming the CPU's 182 and 184 (in accordance with well-known programming principles) to produce that sequence.

Figure 18:
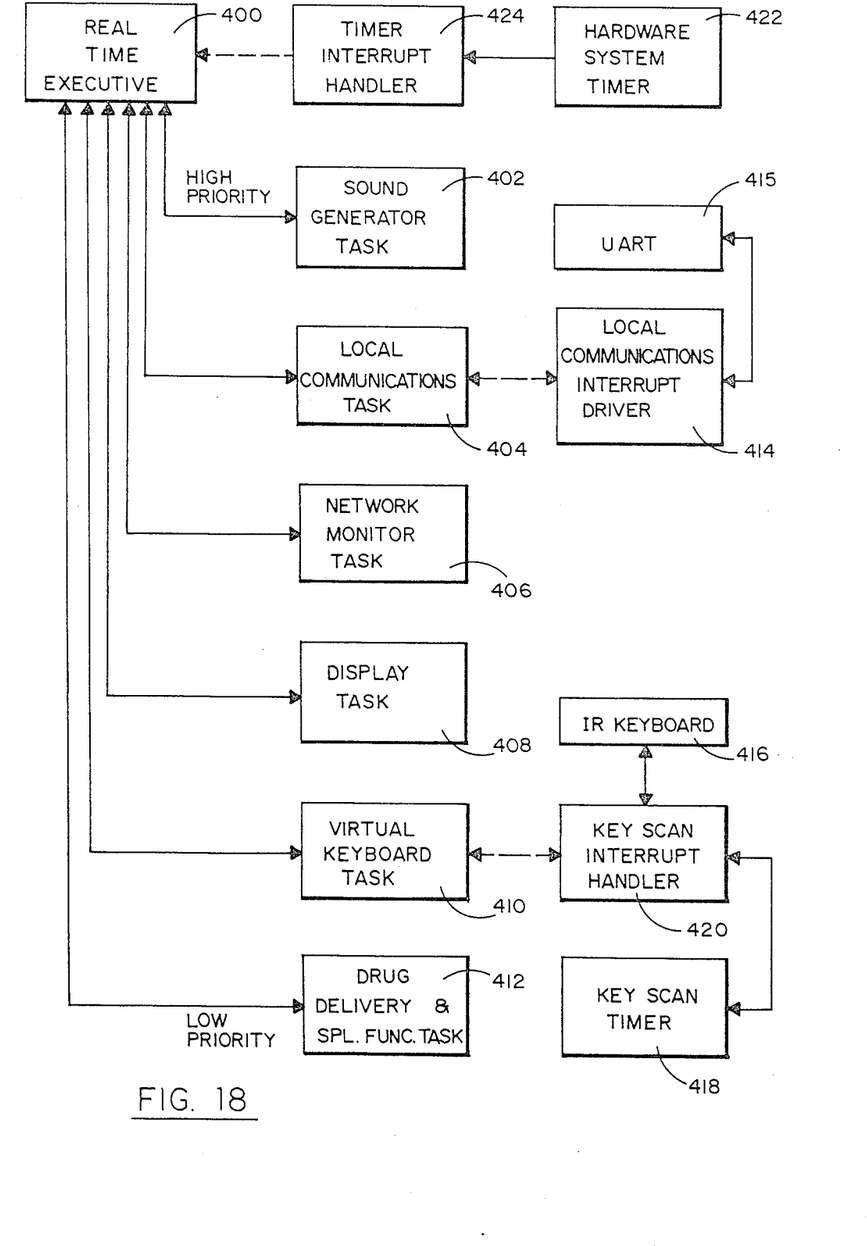
FIG. 18 is a block diagram illustrating the general structure of one program that can be employed with this invention.

FIG. 18 depicts the general structure of such a program. An executive routine 400 normally polls a series of task routines 402 through 412 on a rotating basis to perform the corresponding tasks in descending order of priority as the need for them arises. When the executive finds an active task, control passes to that task routine until it is completed, after which control returns to the executive.

The sound generation task 402 produces predetermined tones or sequences of tones when flagged by other tasks, e.g. in the event of an alarm, keystroke or the like.

The communication task 404 directs the sending and receiving of messages between the central management unit 14 and the modules 16 through 22. It is activated by a communications interrupt drive 44 whenever (periodically or as a result of a physical event) an update or other message is ready to be passed between the unit 14 and the modules. The communication task 404 then controls the routing of messages to and from a UART (universal asynchronous receiver/transmitter) 415 which handles the actual transmission of messages on lines 160 through 166.

The network monitor task 406 monitors the modules 16 through 22 and manages changes in their status. This monitoring is accomplished by requesting the internal status of each module over lines 160 through 166 (via the communication task) one at a time. Whenever a change in status is detected, the changes are saved in the corresponding status buffer. If the change in status is for an attentioned device, the change is sent to the drug delivery task as well.

The display task 408 operates on a list of predefined display commands usually sent by the drug delivery task. Each display command performs one function (i.e. drawing a line, a box, or a point) and an entire display is defined by combining many functions into a display list.

The virtual keyboard task 410 processes keying information from the IR keyboard 416 to determine the locations at which the touch screen 74 is being touched. The IR keyboard 416 made up of the phototransistors 90 is continuously scanned by a key scan timer 418. When the screen 74 is touched, a key scan interrupt handler 420 activates the virtual keyboard task 410. The keyboard task 410 then determines whether the touched location is a valid key location in the current configuration of the display, and what key event it represents. When a valid keypress is recognized, a key beep is requested from the sound task and the key event is passed to the drug delivery task.

The drug delivery and special function task 412 responds to certain system events (i.e. key presses, communication messages, timer timeouts, etc.) by requesting display updates/changes, setting up timers, etc. This task actually controls the inputting of infusion parameters to the modules, performs range checking, and sends the new parameters to the appropriate module via the communication task.

Most of the tasks 402 through 412 perform certain routines at predetermined time intervals. For this purpose, a hardware system timer 422 causes a timer interrupt handler to produce timer interrupts at regular intervals. Each timer interrupt decrements a set of timing variables in the executive routine 400. Each timing variable is individually initialized to a selected value by a task. When a variable is decremented to zero, the executive routine 400 causes the relevant task to initiate the action called for by the expiration of that particular time period.

We claim:

1. A portable modular infusion pump system comprising:
   (a) a central management unit;
   (b) a plurality of modules; and
   (c) connection means on each of said modules and on said management unit for releasably structurally and electrically connecting said modules to each other and to said central management unit to form a stack of modules extrending from said central management unit;
   (d) said modules being positionable in said stack in any order at any time during operation of said system, and being detachable from said stack at any time during such operation, and
   (e) said modules including communication means for transmitting to said central management unit through said electrical connection information regarding their operation;
   (f) at least one of said modules being a pump module including an infusion pump and internal control means for controlling the same, said control means being programmable by said central management unit but arranged to operate said infusion pump independently of said central management unit in accordance with a program established by said central management unit; and
   (g) said central management unit including means for programming said internal control means and for receiving and displaying information from said modules concerning their operation.

2. The system of claim 1, in which one of said modules is permanently connected to said central management unit.

3. The system of claim 1, in which said detachable modules include:
   (i) extendable connecting means for mechanically and electrically interconnecting the module with an adjacent one;
   (ii) said connecting means including contact pins adapted to mate with corresponding contact pins on an adjacent module when said connecting means are extended, and a guide pin adapted to mate with a corresponding recess in said adjacent module when said connecting means are extended, whereby said module and said adjacent module are mechanically interlocked when they are electrically connected by the extension of said connecting means; and
   (iii) said connecting means being fully retractable into the housing of said module when said module and said adjacent module are disconnected from each other.

4. The system of claim 1, in which said detachable modules include:
   (i) module microprocessor means programmable by said central management unit for controlling operational parameters of said infusion pump;
   (ii) said module microprocessor means being programmed to store infusion volume history data from the operation of said infusion pump and to transmit the same to said central management unit.

5. The system of claim 4, in which said module microprocessor means further control a display of operational parameters of said infusion pump and of alarm conditions in said module independently of said central management unit.

6. The system of claim 1, in which said central management unit includes:
(i) central microprocessor means for cyclically receiving operational information from said modules, and displaying said information on demand;
(ii) said central microprocessor means also being programmed to receive operational parameters from an operator and to transmit the same to a selected module to program said module.

7. The system of claim 6, in which said central microprocessor means are further programmed to store operational information from each of said modules at predetermined intervals so as to provide an operational history of each of said modules.

8. The system of claim 1, said central management unit further comprising microprocessor means programmed to cyclically interrogate said modules individually, and display operational information therefrom, in the order of their position in the stack but to record operational information from said modules in accordance with identifying indicia supplied by said modules.

9. The system of claim 8, further including:
(h) identity-assigning means in said central management unit for supplying identifying indicia to each module in said stack when said assembly is activated; and
(i) alarm means in said central management unit for indicating an alarm condition when said central management unit fails to recognize said identifying indicia in one of the modules of the stack or fails to cyclically communicate with one of the modules in the stack.

10. The system of claim 1, in which said pump modules include:
(i) delay means programmable by said central management delaying the start of the module's operation to a predetermined time, and
(ii) alarm means for monitoring predetermined parameters of said pump module and for indicating an alarm condition upon detecting parameter values which would interfere with the onset of the programmed operation of said module at said predetermined time.

11. The system of claim 1, further comprising a sensing module connectable into said stack, said sensing module including communication means for conveying physiological information to said central management unit, and said central management unit including microprocessor means programmed to reprogram at least one of said pump modules in response to said information.

12. The system of claim 1, in which said detachable modules each have first and second sets of electrical contacts, said first set of contacts on each module being adapted to engage said second set of the module above it when said modules are stacked; said first and second sets being electrically interconnected within each of said modules in such a manner that each contact of said first set in the topmost module of the stack is operatively connected to a module occupying a predetermined position in said stack, regardless of the order in which said modules are stacked.

13. The system of claim 1, further comprising an IV stand for supporting said stack, said IV stand having support means for supporting IV bottles, and guide means for retaining cannulae connecting said IV bottles and said modules in a relationship where the length of the path followed by said cannulae between said IV bottles and said modules is generally equal regardless of the position of said module in said stack.

14. The system of claim 1, in which said programming and displaying means include:
(i) attention means on each pump module for causing said programming and displaying means to accept and display data relating to said module;
(ii) means on said central management unit for entering operational parameters for said module and communicating the same to said module;
(iii) means in said module for storing operational data transmitting the same to said central management unit; and
(iv) means in said central management unit for storing said operational data for all of said pump modules, updating said stored data upon transmission of data by said modules, and displaying the operational data for the module whose attention means have most recently been actuated.

* * * * *